(12) United States Patent
Tokunaga

(10) Patent No.: US 8,058,296 B2
(45) Date of Patent: Nov. 15, 2011

(54) TREATMENT AND PREVENTION OF DELETERIOUS EFFECTS ASSOCIATED WITH ALCOHOL CONSUMPTION

(76) Inventor: Richard Tokunaga, Honolulu, HI (US)

( * ) Notice: Subject to any disclaimer, the term of this patent is extended or adjusted under 35 U.S.C. 154(b) by 298 days.

(21) Appl. No.: 12/323,098

(22) Filed: Nov. 25, 2008

(65) Prior Publication Data

US 2010/0130573 A1    May 27, 2010

(51) Int. Cl.
*A61K 31/426* (2006.01)
(52) U.S. Cl. ..................................................... 514/370
(58) Field of Classification Search .................. 514/370, 514/562
See application file for complete search history.

(56) References Cited

U.S. PATENT DOCUMENTS

| | | |
|---|---|---|
| 4,096,266 A | 6/1978 | Itil |
| 5,021,582 A | 6/1991 | Ballester-Rodes et al. |
| 5,352,688 A | 10/1994 | Kaminski |
| 5,364,616 A | 11/1994 | Singer et al. |
| 5,453,428 A | 9/1995 | Kaminski |
| 5,496,836 A | 3/1996 | Di Rocco et al. |
| 5,593,696 A | 1/1997 | McNally et al. |
| 5,650,421 A | 7/1997 | Titus et al. |
| 5,759,539 A | 6/1998 | Whitmire |
| 5,817,340 A | 10/1998 | Roche et al. |
| 6,090,412 A | 7/2000 | Hashimoto et al. |
| 6,552,047 B2 | 4/2003 | Garvey et al. |
| 6,926,907 B2 | 8/2005 | Plachetka |
| 7,094,414 B2 | 8/2006 | Nakata et al. |
| 2001/0043959 A1 | 11/2001 | Gelber et al. |
| 2004/0010021 A1 | 1/2004 | Racz et al. |
| 2005/0203105 A1 | 9/2005 | Tan et al. |
| 2005/0271754 A1* | 12/2005 | Cochrane ..................... 424/750 |

FOREIGN PATENT DOCUMENTS

| | | |
|---|---|---|
| WO | WO 95/01792 | 1/1995 |
| WO | WO 2004/016268 | 2/2004 |
| WO | WO 2007/000038 | 1/2007 |

* cited by examiner

*Primary Examiner* — Jennifer M Kim
(74) *Attorney, Agent, or Firm* — Biotech Beach Law Group PC

(57) ABSTRACT

The present invention provides to methods and compositions that treat or prevent deleterious effects associated with alcohol consumption including alcohol-induced flush reaction and hangover. The methods and compositions include famotidine and optionally succinic acid. The present invention further demonstrates compositions that include famotidine are effective at treating symptoms associated with a flush reaction in subjects that are not significantly responsive to treatments with the H1 antagonist loratidine or the H2 antagonist cimetidine.

4 Claims, 2 Drawing Sheets

TREATMENT AND PREVENTION OF DELETERIOUS EFFECTS ASSOCIATED WITH ALCOHOL CONSUMPTION

TECHNICAL FIELD OF THE INVENTION

The present invention relates to the prevention or treatment of effects associated with alcohol consumption and more specifically to methods and compositions for the treatment or prevention of alcohol-induced flush reaction and hangover.

BACKGROUND OF THE INVENTION

Metabolism of alcohol involves a two step enzymatic reaction. First, alcohol is oxidized to acetaldehyde by alcohol dehydrogenase. Second, the acetaldehyde is oxidized to acetic acid by acetaldehyde dehydrogenase and glutathione. Acetic acid is then transported to the muscles and adipose tissue where it is further broken down into carbon dioxide and water. Thus, the rate at which alcohol is metabolized to acetic acid depends in part upon the balance of both alcohol dehydrogenase and acetaldehyde dehydrogenase. This balance is important because although alcohol is toxic to the body, acetaldehyde is actually more toxic than alcohol.

Polymorphisms in the acetaldehyde dehydrogenase gene correlate significantly to particular populations, such as those having Asian ancestry and even more significantly to those having Japanese ancestry. These polymorphisms frequently result in slowed conversion of acetaldehyde to acetic acid. Accordingly, without significant slowing of alcohol dehydrogenase activity, acetaldehyde begins to build up in the body. Rapid accumulation of acetaldehyde causes redness in the skin, primarily along the face and limbs. This condition is referred to as alcohol-induced flush reaction, also known as Asian flush.

A combination treatment for controlling alcohol-induced flush reaction is proposed in published U.S. patent application Ser. No. 11/009,559. Specifically, the authors propose a combined treatment prior to imbibing in alcohol, the treatment including administering both an H1 receptor histamine antagonist and a H2 receptor histamine antagonist. The proposed H1 receptor antagonists include terfenadine, astemisole and fenoxifene. The proposed H2 receptor antagonists included cimetidine, famotidine, nizatidine and ranitidine. Such treatments do not address the conversion of alcohol to acetic acid but instead propose to competitively antagonize H1 and H2 histidine receptors while in circulation, which temporarily reduces the appearance of symptoms. However, the proposed treatments suffer from two drawbacks. First, many that suffer from alcohol-induced flush reaction do not respond to many of the proposed antagonists, which indicates the antagonists are not interchangeable. Second, in some instances temporarily masking symptoms may lead to increased alcohol consumption, which may intensify deleterious effects once temporary relief ends.

Although alcohol-induced flush reaction is typically associated with redness that occurs relatively shortly after consumption of alcohol, the build up of acetaldehyde also contributes to hangover, which is often felt by many the morning after alcohol consumption. Common hangover effects include headache, nausea, dizziness, fatigue, thirst, tension, anxiety, paleness, tremor and perspiration. It is commonly believed that black coffee or further consumption of alcohol in the morning reduces the symptoms; however, the effectiveness varies across individuals.

Accordingly, there remains a need to develop new methods and compositions for the treatment and prevention of deleterious effects associated with alcohol consumption.

SUMMARY OF THE INVENTION

The present invention addresses deficiencies in methods and compositions for the treatment or prevention of deleterious effects associated with alcohol consumption and provides related benefits. This is accomplished by the compositions and their administration as provided herein.

In one aspect of the present invention a composition for the prevention or reduction of deleterious effects associated with alcohol consumption is provided including an effective amount of each of famotidine and succinic acid and a pharmaceutically acceptable carrier. The composition is effective at preventing or reducing alcohol-induced flush reaction and hangover. The composition is particularly useful for subjects that do not significantly respond to treatments such as the H1 receptor antagonist loratidine or the H2 receptor antagonist cemetidine.

In another aspect of the present invention, a method for preventing or reducing alcohol-induced flush reaction and hangover in a human is provided including administering to the human an effective amount of a composition including famotidine and succinic acid with a pharmaceutically acceptable carrier prior to imbibing in alcohol. Famotidine may be provided as the sole histamine receptor antagonist. The method may be particularly desired for humans that do not significantly respond to loratidine and/or cemetidine.

In another aspect of the present invention a method for the prevention or reducing alcohol-induced flush reaction in a human is provided including administering to the human an effective amount of famotidine as a sole histamine receptor antagonist prior to imbibing in alcohol and optionally succinic acid.

In another aspect of the present invention a method for treating alcohol-induced flush reaction in a human is provided including administering to a human in need thereof an effective amount of famotidine and a pharmaceutically acceptable carrier.

DETAILED DESCRIPTION OF THE INVENTION

The present invention provides methods and compositions for the treatment, prevention or amelioration of symptoms associated with consumption of alcohol. In some embodiments, the present invention treats, prevents or reduces hangover. In some embodiments, the present invention treats, prevents or reduces symptoms associated with alcohol-induced flush reaction. The objects of the present invention are accomplished by providing an effective amount of famotidine, succinic acid, or a combination thereof. Administration preferably occurs prior to imbibing in alcohol; however, in some embodiments the treatment is provided after or during imbibing in alcohol.

Figure 1:
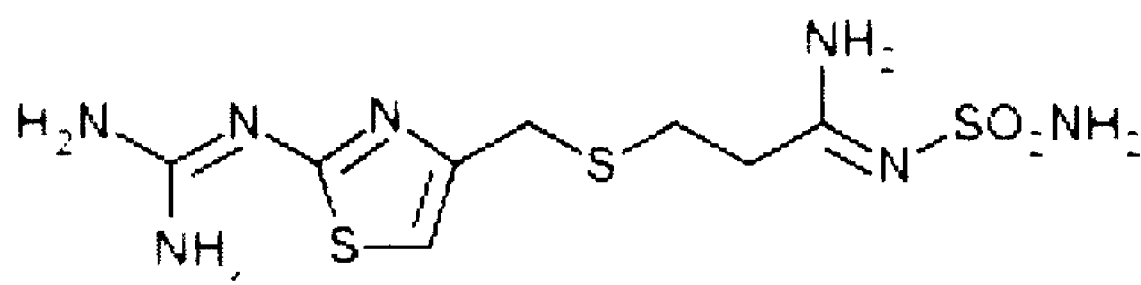
FIG. 1 is a structural formula of famotidine.

The preferred composition and methods of the present invention provide a sole histamine receptor antagonist, famotidine. The term "sole histamine receptor antagonist" refers to the use of famotidine without inclusion of an additional H1 or H2 receptor antagonist. Famotidine is a white to pale yellow crystalline compound that is freely soluble in glacial acetic acid, slightly soluble in methanol, very slightly soluble in water, and practically insoluble in ethanol. It has a molecular weight of 337.43; an empirical formula of $C_8H_{15}N_7O_2S_3$; and its structural formula is provided as FIG. 1. The chemical name for famotidine is N'-(aminosulfonyl)-3-([2diaminomethyleneamino)-4-thiazolyl]methylthio)propanamidine.

Like cimetidine, famotidine is a member of compounds referred to histamine H2 antagonists (also referred to as histamine-2 blockers). H2 antagonists selectively block histamine H2 receptors and not histamine H1 receptors. Famotidine is commercially available under the brand names PEPCID and MYLANTA and is believed to decrease the amount of acid the stomach produces. Famotidine is advertised as a treatment for ulcers in the stomach and intestines, Zollinger-Ellison syndrome, gastroesophageal reflux disease (GERD), and other conditions associated with the presence of acid in the esophagus, causing heartburn. Famotidine is commercially available in doses of 20 mg and 40 mg.

The examples provided herein demonstrate a series of exemplary studies that demonstrate famotidine is effective as a preventative treatment against symptoms associated with alcohol-induced flush reaction. In addition, the studies demonstrate famotidine is highly effective at low dose; whereas cimetidine (another H2 antagonist) was minimally effective even at a higher dose. Thus the treatment effects of famotidine are not believed to be associated with all H2 antagonists.

Although famotidine is effective at reducing alcohol-induced flush reaction, when combined with succinic acid the composition is also effective at preventing or reducing hangover. Famotidine may provide instant, near term or temporary relief and succinic acid may provide prolonged relief. Accordingly, in some embodiments famotidine and succinic acid are provided with a pharmaceutically effective carrier for the prevention or treatment of deleterious effects associated with alcohol consumption. The composition may reduce immediate deleterious effects such as redness and may reduce or prevent hangover.

Hangovers are believed to be multi-causal. First, ethanol is a diuretic, which increases urine production, and thus has a dehydrating effect. Dehydration leads to symptoms such as headache, dry mouth and lethargy. Second, NADH is accumulated from the metabolism of alcohol from alcohol dehydrogenase enzyme. Excess NADH can slow down gluconeogenesis in the liver, which causes hypoglycemia. Third, when ethanol is metabolized it is converted to acetaldehyde. Acetaldehyde dehydrogenase breaks acetaldehyde into acetic acid. Acetylaldehyde is about 10 to 30 times more toxic than ethanol.

Figure 2:
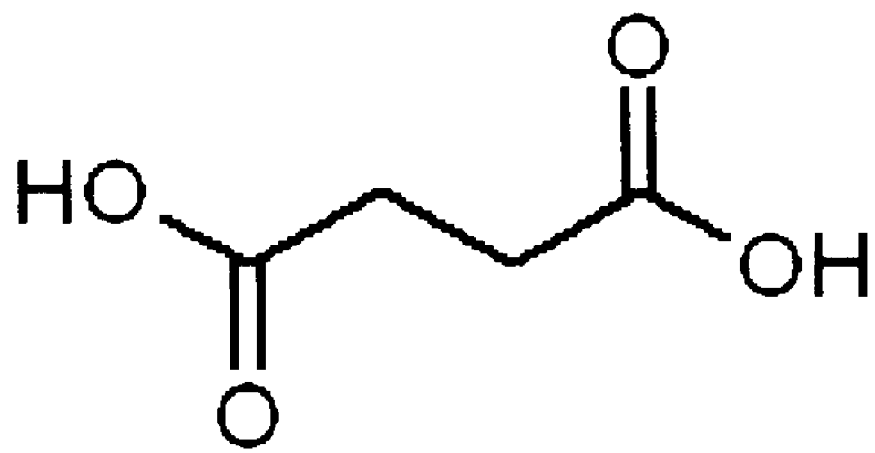
FIG. 2 is a structural formula of succinic acid.

Succinic acid, also known as butandioic acid or ethane-1, 2-dicarboxylic acid, has the formula $C_4H_6O_4$ and the structure of such is provided as FIG. 2. At room temperature succinic acid is a solid that forms colorless, odorless crystals. The carboxylate anion is referred to as succinate, which is a component in the citric acid cycle. Esters of succinic acid are referred to as alkyl succinates. Succinic acid is commercially available as dietary supplement. Though non-limiting, it is believed that the addition of succinic acid will accelerate the decomposition of acetaldehyde. This is believed to be due at least in part to its role in the citric acid cycle.

The compositions provided herein, namely famotidine and/or succinic acid are administered in an effective amount. The term "effective amount" as used herein refers to the amount of each active ingredient, which provides a beneficial effect. With respect to famotidine, an effect amount significantly reduces symptoms associated with alcohol-induced flush reaction, such as decreased redness that is easily observable compared to no treatment or in some instances compared to treatment with cimetidine or loratidine. Preferably, increased redness is not visually observed at the face, limbs or torso. With respect to succinic acid, the effective amount prevents or reduces one or more hangover symptoms. The effective amount may vary depending on route of administration and between individuals. In some embodiments the effective amount is less than 20 mg for each of famotidine and succinic acid. For instance, the present invention provides a study wherein 10 mg of famotidine significantly prevents redness while imbibing in alcohol.

The present invention includes 10 mg as an effective amount of famotidine in the prevention or treatment of alcohol-induced flush reaction or when used in combination with succinic acid; however, lower doses such as about 1 mg to nearly 10 mg are also encompassed by the present invention. Succinic acid may be provided any effective amount such as between about 1 mg and about 500 mg. In some embodiments, succinic acid is provided in 10 mg. In other embodiments, succinic acid is provided between 20 mg and 100 mg; 100 mg and 250 mg; 250 mg and 500 mg; or 500 mg and 750 mg. In a preferred embodiment 200 mg of succinic acid was effective at reducing or eliminating hangover when provided in combination with 10 mg of famotidine.

Although the methods of the present invention encompass any suitable administration technique known in the pharmaceutical arts, in the preferred embodiment, the compositions are administered orally. Oral administration may involve providing famotidine and/or succinic acid in any suitable form such as pill, capsule, oral syrup and the like. Techniques for the formation of such compositions are well known in the pharmaceutical arts and can be found in a variety of pharmaceutical textbooks and publications, such as *Remington's Pharmaceutical Sciences* (Mack Publishing Co., Eaton, Pa.), the contents of which are herein incorporated by reference in its entirety. The compositions typically involve mixing the active ingredient or a salt thereof in the presence of a suitable carrier, also referred to as a pharmaceutically acceptable carrier. Thus, the active ingredients may be mixed with diluents, excipients or other carriers used in the pharmaceutical arts. Further, active ingredients may be mixed with solubilizers, stabilizers, buffering agents, coloring agents, flavoring agents, emulsions and the like as performed and known in pharmaceutical practice.

EXAMPLES

Example 1

Figure 3A:
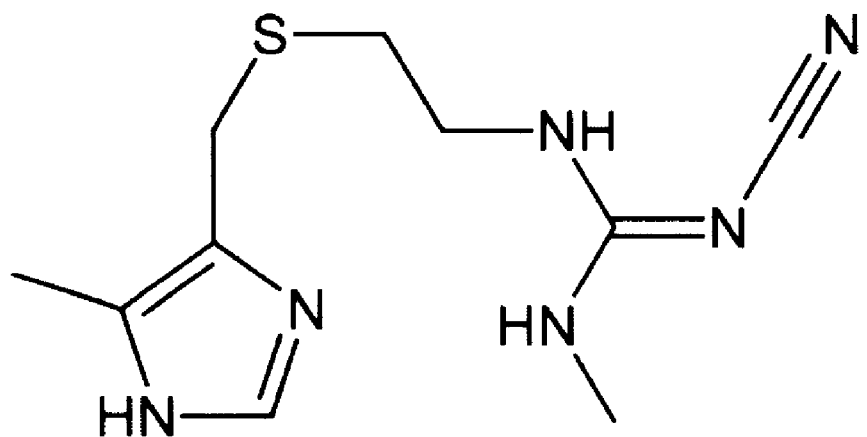
FIG. 3A is a structural formula of cimetidine.
Figure 3B:
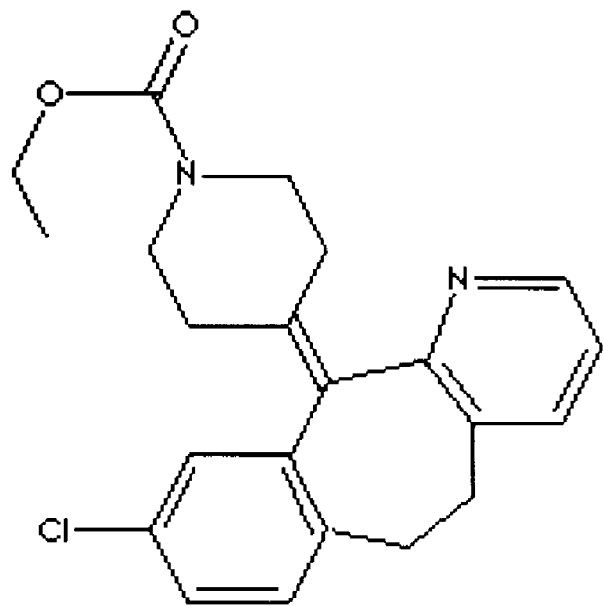
FIG. 3B is a structural formula of loratidine.

Prevention of Alcohol-Induced Flush Reaction in Subjects Treated with Famotidine The following examples demonstrate the prevention or reduction of symptoms associated with alcohol-induced flush reaction. As control, each subject was tested without treatment. As a second control, each subject was treated with either loratidine (an H1 antagonist) or cimetidine (an H2 antagonist). Cimetidine is shown as FIG. 3A and loratidine is shown as FIG. 3B. Each subject was also treated with famotidine in a subsequent study. The results are summarized in tables 1-4 that follow.

Subject 1: Patient LB

Patient LB is a female, is 27 years old and weighs 115 lbs. She is not taking any medications presently. There is no other medical history of consequence.

Ms. LB drinks alcohol socially on occasion, usually in the form of Vodka. After imbibing several glasses of Vodka, however, LB consistently finds that she has a flushing of the face and torso. Via her own history and symptoms, Patient LB is demonstrably susceptible to alcohol-induced flushing.

To examine potential treatment with loratidine (an H1 histamine antagonist), Patient LB underwent a protocol of medical treatment to control alcohol-induced facial flushing. In accordance with the treatment protocol about forty five (45) minutes before the next social occasion when she was expecting (or intending) to imbibe any alcoholic beverage, LB orally self-administered 20 mg of loratadine (CLARITIN) in tablet form. Subsequently/after drinking 3 alcoholic beverages over about three to four hours time, LB experienced a facial flushing reaction and an increased heart rate as a result of her intake of alcohol. Thus, the flushing blockade remained ineffective with the use of loratidine by itself.

To examine potential treatment with famotidine, Patient LB again underwent a protocol of medical treatment to control alcohol-induced flushing. In accordance with the treatment protocol, about forty five (45) minutes before the next social occasion when she was expecting (or intending) to imbibe Vodka or any other alcoholic beverage, LB orally self-administered 10 mg of famotidine in chewable tablet form. Subsequently, after then drinking 2-3 glasses of Vodka over several hours time, LB experienced no flushing reactions, either of the face or of the torso. Thus, the flushing blockade never became ineffective over the duration of the social drinking occasion. In addition, LB experienced no undesired side-effects whatsoever; in particular. LB felt no drowsiness or sedation over the entire duration of the flushing blockade and the social drinking occasion.

Thus, famotidine but not loratidine provided an effective preventative treatment against alcohol-induced flush reaction for Patient LB.

Subject 2: Patient CA

Patient CA is a male, is 29 years old and weighs 165 lbs. He is taking no medication presently and also has no prior medical history of consequence.

Mr. CA drinks alcohol socially, usually in the form of mixed cocktails known as "Vodka/RedBull", after imbibing several alcoholic cocktails; however. CA routinely finds that he has undergone a marked flushing of the face. Via his own history and symptoms, Patient CA is demonstrably susceptible to alcohol-induced flushing.

To examine potential treatment with cimetidine, Patient CA then underwent a protocol of medical treatment to control alcohol-induced facial flushing. In accordance with the treatment protocol, about forty five (45) minutes before the next social occasion when he was expecting (or intending) to imbibe any alcoholic beverage, CA orally self-administered 300 mg of cimetidine (TAGAMET) in tablet form. Subsequently/after drinking 2 alcoholic beverages over about three hours time, CA still experienced a facial flushing reaction and an increased heart rate as a result of his intake of alcohol. Thus, the flushing blockade remained generally ineffective with the use of cimetidine by itself.

To examine potential treatment with famotidine, Patient CA also underwent a protocol of medical treatment to control alcohol-induced flushing. In accordance with the treatment protocol, about forty five (45) minutes before the next social occasion when she was expecting (or intending) to imbibe mixed cocktails or any other alcoholic beverage, CA orally self-administered 10 mg of famotidine in chewable tablet form. Subsequently, after then drinking cocktails over a time period of about 4 hours duration, CA experienced no flushing reactions of the face. Thus, the flushing blockade never became ineffective over the duration of the social drinking occasion. In addition, CA experienced no undesired side-effects whatsoever; in particular, CA felt no drowsiness or sedation over the entire duration of the flushing blockade and the social drinking occasion.

The effects were slightly less aggressive when taking cimetidine alone compared to no treatment but the present study shows that the use of famotidine proved to be much more effective than cimetidine or no treatment.

Subject 3: Patient YT

Patient YT is a female, is 61 years old and weighs 155 lbs. She is taking Ambien (by prescription) presently. She has no other medical history of consequence.

Ms. YT drinks alcohol socially on occasion usually in the form of wine. By her own admission, YT typically drinks ten (10) or more glasses of wine per week. After imbibing wine, however, YT consistently has headaches and has a marked flushing of the face and torso. Via her own history and symptoms. Patient YT is clearly susceptible to alcohol-induced flushing.

To examine potential treatment with loratadine, Patient YT underwent a protocol of medical treatment to control alcohol-induced facial flushing. In accordance with the treatment protocol, about forty five (45) minutes before the next social occasion when she was expecting (or intending) to imbibe any alcoholic beverage, YT orally self-administered 20 mg of loratadine (CLARITIN) in tablet form. Subsequently/after drinking 3 alcoholic beverages over about three to four hours time, YT experienced a facial flushing reaction and an increased heart rate as a result of her intake of alcohol. Thus, the flushing blockade remained ineffective with the use of loratadine by itself.

To examine potential treatment with famotidine, Patient YT underwent a protocol of medical treatment to control alcohol-induced flushing. In accordance with the treatment protocol, about forty five (45) minutes before the next social occasion when she was expecting (or intending) to imbibe wine or any other alcoholic beverage, YT orally self-administered 10 mg of famotidine in chewable tablet form. Subsequently, after then drinking multiple glasses of wine over four (4) hours time, YT experienced no flushing reactions of the face or of the torso. In addition, YT experienced no undesired side-effects whatsoever; in particular, YT felt no drowsiness or sedation over the entire duration of the flushing blockade and the social drinking occasion.

Thus, famotidine but not loratidine provided an effective treatment in the prevention of alcohol-induced flush reaction for Patient YT.

Subject 4: Patient MC

Patient MC is a female, is 24 years old and weighs 110 lbs. She is taking birth control medication. She has no other medical history of consequence.

Ms. MC drinks alcohol socially on occasion, usually in the form of beer and tequila. After imbibing several glasses of beer or alcohol, however, MC routinely finds that a flushing of the face results and nausea. Via her own history and symptoms, Patient MC is susceptible to alcohol-induced facial flushing.

To examine potential treatment with cimetidine, Patient MC underwent a protocol of medical treatment to control alcohol-induced facial flushing. In accordance with the treatment protocol, about forty five (45) minutes before the next social occasion when she was expecting (or intending) to imbibe any alcoholic beverage, MC orally self-administered 300 mg of cimetidine (TAGAMET) in tablet form. Subsequently/after drinking 2 alcoholic beverages over about a two hours time, MC still experienced a facial flushing reaction, increased heart rate, as well as a headache as result of his intake of alcohol. Thus, the flushing blockade remained generally ineffective with the use of cimetidine by itself.

To examine potential treatment with famotidine. Patient MC underwent a protocol of medical treatment to control alcohol-induced facial flushing. In accordance with the treatment protocol, about forty five (45) minutes before the next social occasion when she was expecting (or intending) to imbibe beer or any other alcoholic beverage, MC orally self-administered 10 mg of famotidine in chewable tablet form. Then subsequently, in spite of drinking 2 ounces of tequila and 5 glasses of beer over more than six (6) hours drinking time, MC nevertheless experienced no facial flushing reaction. Thus, the flushing blockade never became ineffective over the more than six hour duration of MC's social drinking. In addition, MC experienced no undesired side-effects whatsoever; in particular, MC felt no drowsiness or sedation over the entire duration of the flushing blockade and the social drinking occasion.

In summary, the effects were slightly less aggressive when taking cimetidine alone when compared to no treatment but the present study shows that the use of famotidine proved to be much more effective than cimetidine to prevent alcohol induced flushing for Patient MC.

Subject 5: Patient CJR

Patient CJR is a male, is 30 years old and weighs 185 lbs. He has no other medical history of consequence.

Mr. CJR drinks alcohol socially on occasion, but without preference as to alcoholic form. After imbibing only a few alcoholic drinks, however, CJR consistently finds that he has a flushing of the face and also experiences nasal congestion. Via his own history and symptoms, Patient CJR is demonstrably susceptible to alcohol-induced flushing.

To examine potential treatment with loratidine, Patient CJR underwent a protocol of medical treatment to control alcohol-induced facial flushing. In accordance with the treatment protocol, about forty five (45) minutes before the next social occasion when he was expecting (or intending) to imbibe any alcoholic beverage, CJR orally self-administered 20 mg of loratadine (CLARITIN) in tablet form. Subsequently/after drinking 1 alcoholic beverage over a one hour time CJR experienced a facial flushing reaction and an increased heart rate as a result of his intake of alcohol. Thus, the flushing blockade remained ineffective with the use of loratadine by itself.

To examine potential treatment with famotidine, Patient CJR underwent a protocol of medical treatment to control alcohol-induced flushing. In accordance with the treatment protocol, about forty five (45) minutes before the next social occasion when he was expecting (or intending) to imbibe any alcoholic beverage, CJR orally self-administered 10 mg of famotidine in chewable tablet form. Subsequently, after drinking 5 alcoholic beverages over about five hours time, CJR experienced neither a facial flushing reaction nor any nasal congestion. Thus, the flushing blockade remained effective over the five hours time of his social drinking occasion. In addition, CJR experienced no undesired side-effects whatsoever; in particular, CJR felt no drowsiness or sedation over the duration of the flushing blockade.

However, on this occasion, CJR chose to continue his consumption of alcoholic beverages beyond six drinks and for an extended period of time greater than six hours. The duration of effective facial flushing blockade did not extend beyond the initial five hours time period; and CJR showed specific symptoms as a result of him continuing intake of alcohol, including facial flushing, an increased heart rate, and nasal congestion.

Thus, famotidine but not loratidine provided an effective treatment in the prevention of alcohol-induced flush reaction for Patient CJR and the protective effect of famotidine dissipated after a period of about five hours.

TABLE 1

Initial Measurements No Treatment & No Alcohol

| Subject | Initials | Sex | Weight (lbs) | Temp (F.) | Heart rate |
|---|---|---|---|---|---|
| 1 | LB | F | 115 | 97.4 | 74 |
| 2 | CA | M | 165 | 98.1 | 84 |
| 3 | YT | F | 145 | 97.7 | 78 |
| 4 | MC | F | 110 | 96.5 | 72 |
| 5 | CJR | M | 185 | 97.1 | 81 |

TABLE 2

Control Measurements Alcohol Exposure without Treatment

| Subject | Initials | Sex | Treatment | Temp (F.) | Heart rate |
|---|---|---|---|---|---|
| 1 | LB | F | None | 97.1 | 89 |
| 2 | CA | M | None | 98.0 | 97 |
| 3 | YT | F | None | 97.5 | 93 |
| 4 | MC | F | None | 97.1 | 87 |
| 5 | CJR | M | None | 96.9 | 91 |

TABLE 3

Control Treatment (Loratidine or Cimetidine) with Alcohol

| Subject | Initials | Sex | Treatment | Temp (F.) | Heart rate |
|---|---|---|---|---|---|
| 1 | LB | F | Loratidine | 97.1 | 89 |
| 2 | CA | M | Cimetidine | 98.0 | 97 |
| 3 | YT | F | Loratidine | 97.5 | 93 |
| 4 | MC | F | Cimetidine | 97.1 | 87 |
| 5 | CJR | M | Loratidine | 96.9 | 91 |

TABLE 4

Famotidine Treatment with Alcohol

| Subject | Initials | Sex | Treatment | Temp (F.) | Heart rate |
|---|---|---|---|---|---|
| 1 | LB | F | Famotidine | 97.3 | 77 |
| 2 | CA | M | Famotidine | 98.2 | 82 |
| 3 | YT | F | Famotidine | 97.4 | 84 |
| 4 | MC | F | Famotidine | 97.1 | 78 |
| 5 | CJR | M | Famotidine | 97.3 | 83 |

Example 2

Prevention of Alcohol Flush Reaction and Hangover by Administration of Famotidine and Succinic Acid To test whether both alcohol flush reaction and hangover could be prevented four subjects susceptible to both alcohol flush reaction and hangover were given a combination of famotidine and succinic acid prior to imbibing in alcohol. Previous studies with famotidine alone did not appear to significantly reduce or eliminate symptoms associated with hangover. Each subject was given 10 mg famotidine and 200 mg succinic acid prior to imbibing in alcohol. Afterwards each ingested sufficient alcohol that would ordinarily result in both flush reaction and hangover. None of the four tested individuals indicated flush symptoms or symptoms associated with hangover. Thus, the results show the combination of both famotidine and succinic acid prevents alcohol flush reaction and hangover.

The present invention is not to be restricted in scope not limited in form except by the claims attached hereto.

What is claimed is:

1. A method of treating alcohol induced flush reaction and alcohol hangover in a human, wherein the alcohol induced flush reaction is not substantially reduced or prevented through administration of a sole histamine receptor antagonist of loratadine or cemetidine, the method comprising administering to the human in need thereof a therapeutically effective amount of a composition consisting essentially of famotidine and succinic acid.

2. The method according to claim 1, wherein the effective amount is 10 mg.

3. The method according to claim 1, wherein the effective amount is 20 mg.

4. The method according to claim 1, wherein the famotidine is orally administered.

* * * * *